(12) United States Patent
Mosdzianowski et al.

(10) Patent No.: US 10,532,115 B2
(45) Date of Patent: Jan. 14, 2020

(54) HEATSEAL

(71) Applicant: GE Healthcare Limited, Buckinghamshire (GB)

(72) Inventors: Christoph Mosdzianowski, Loncin (BE); Philippe Dumont, Loncin (BE); Sali Kuci, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 531 days.

(21) Appl. No.: 15/117,847

(22) PCT Filed: Mar. 30, 2015

(86) PCT No.: PCT/EP2015/056919
§ 371 (c)(1),
(2) Date: Aug. 10, 2016

(87) PCT Pub. No.: WO2015/144935
PCT Pub. Date: Oct. 1, 2015

(65) Prior Publication Data
US 2017/0007728 A1    Jan. 12, 2017

(30) Foreign Application Priority Data

Mar. 28, 2014    (GB) .................................. 1405591.7

(51) Int. Cl.
*A61K 51/12*    (2006.01)
*C07B 59/00*    (2006.01)
(Continued)

(52) U.S. Cl.
CPC ......... *A61K 51/1286* (2013.01); *B01J 19/004* (2013.01); *B29C 65/747* (2013.01);
(Continued)

(58) Field of Classification Search
CPC ........... A61K 51/1282; A61K 51/1286; B29C 57/00; B29C 57/10; B29L 2023/00; B01J 19/0093
See application file for complete search history.

(56) References Cited

U.S. PATENT DOCUMENTS

| | | | |
|---|---|---|---|
| 2,762,421 A * | 9/1956 | Quinche | B29C 57/10 156/198 |
| 4,013,860 A * | 3/1977 | Hosterman | B29C 65/04 156/380.6 |

(Continued)

FOREIGN PATENT DOCUMENTS

WO    2008/128201 A1    10/2008

OTHER PUBLICATIONS

International Search Report and Written Opinion regarding International Application No. PCT/EP2015/056919, dated Jun. 24, 2015, 8 pages.

(Continued)

*Primary Examiner* — Robert F Long
*Assistant Examiner* — Eduardo R Ferrero
(74) *Attorney, Agent, or Firm* — Arent Fox, LLP

(57) ABSTRACT

The present invention relates to systems and methods to facilitate replacement between runs of a kit or cassette from an automated radiosynthesis device located in a hot cell. The method and apparatus of the invention enable automated disconnection of the outlet line by sealing the tubing hermetically by means of heat and by cutting the tubing where it is sealed in such a way that there is no risk of environmental contamination with radioactive material. The invention enables disconnection of the outlet line without manual intervention before opening the shielded enclosure.

31 Claims, 3 Drawing Sheets

(51) Int. Cl.
  *B01J 19/00* (2006.01)
  *B29C 65/74* (2006.01)
  *B65B 5/04* (2006.01)
  *B29C 57/10* (2006.01)
  *B29C 57/00* (2006.01)
  *B29K 101/12* (2006.01)
  *B29L 23/00* (2006.01)

(52) U.S. Cl.
  CPC ............... B65B 5/04 (2013.01); C07B 59/00 (2013.01); *B29C 57/00* (2013.01); *B29C 57/10* (2013.01); *B29K 2101/12* (2013.01); *B29L 2023/00* (2013.01); *C07B 2200/05* (2013.01)

(56) References Cited

U.S. PATENT DOCUMENTS

| | | | | |
|---|---|---|---|---|
| 4,186,292 A * | 1/1980 | Acker | ............... | A61J 1/05 219/769 |
| 4,351,692 A * | 9/1982 | Ouellette | ............... | B29C 57/10 156/153 |
| 4,488,028 A * | 12/1984 | Acker | ............... | B29C 65/04 156/380.4 |
| 4,496,819 A * | 1/1985 | Acker | ............... | B29C 65/04 156/380.4 |
| H000074 H * | 5/1986 | Shiue | ............... | C07H 1/00 536/122 |
| 4,617,386 A * | 10/1986 | Elmaleh | ............... | C07H 15/04 536/122 |
| 5,190,880 A * | 3/1993 | Cassou | ............... | A01N 1/02 422/408 |
| 5,209,800 A * | 5/1993 | Spencer | ............... | A61M 39/146 156/158 |
| 5,345,070 A * | 9/1994 | Hlavinka | ............... | B29C 65/04 156/273.7 |
| 5,397,425 A * | 3/1995 | Ivansons | ............... | B29C 57/10 156/304.2 |
| 5,759,513 A * | 6/1998 | Nakazawa | ............... | A61K 51/0402 422/903 |
| 5,932,178 A * | 8/1999 | Yamazaki | ............... | B01J 19/0046 376/168 |
| 6,392,246 B1 * | 5/2002 | Wiberg | ............... | A61K 51/1282 250/506.1 |
| 6,485,593 B1 * | 11/2002 | Christoffersen | ............... | A61M 39/18 156/157 |
| 6,772,576 B2 * | 8/2004 | Luehr | ............... | B65B 7/14 53/284 |
| 7,326,898 B2 * | 2/2008 | Dozier | ............... | H05B 6/62 156/380.3 |
| 7,976,824 B2 * | 7/2011 | Brown | ............... | C07H 5/02 424/1.11 |
| 8,066,269 B2 * | 11/2011 | Ivansons | ............... | B23K 37/0435 269/152 |
| 8,206,571 B2 * | 6/2012 | Clarke | ............... | G21G 4/00 204/275.1 |
| 8,435,454 B2 * | 5/2013 | Elizarov | ............... | B01J 19/0093 422/130 |
| 2003/0004463 A1 * | 1/2003 | Reilly | ............... | A61K 51/1282 604/124 |
| 2004/0086437 A1 * | 5/2004 | Jackson | ............... | G21G 4/08 422/292 |
| 2005/0085682 A1 * | 4/2005 | Sasaki | ............... | A61K 51/1282 600/4 |
| 2005/0242276 A1 * | 11/2005 | Okazaki | ............... | A61K 51/1282 250/251 |
| 2005/0265906 A1 * | 12/2005 | Najafi | ............... | A61K 51/1282 422/159 |
| 2006/0057062 A1 * | 3/2006 | Trotter | ............... | A61K 51/109 424/1.49 |
| 2006/0188441 A1 * | 8/2006 | Tolmachev | ............... | A61K 51/088 424/1.69 |
| 2006/0245980 A1 | 11/2006 | Kiselev et al. | | |
| 2008/0023135 A1 * | 1/2008 | Ivansons | ............... | A61M 39/146 156/304.2 |
| 2008/0233018 A1 * | 9/2008 | van Dam | ............... | B01J 19/0093 422/159 |
| 2008/0305042 A1 * | 12/2008 | Gacek | ............... | A61K 51/0402 424/1.89 |
| 2010/0282350 A1 * | 11/2010 | Lofving | ............... | B23D 21/006 138/97 |
| 2011/0155274 A1 * | 6/2011 | Zumbrum | ............... | A61M 39/08 138/137 |
| 2014/0251859 A1 * | 9/2014 | Weikart | ............... | A61J 1/00 206/524.9 |

OTHER PUBLICATIONS

GB Search Report regarding GB Application No. 1405591.7, dated Sep. 26, 2014, 3 pages.

* cited by examiner

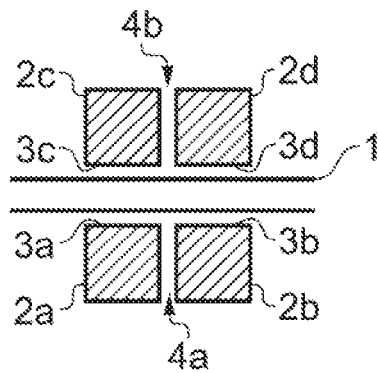
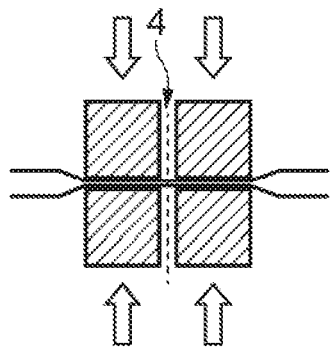
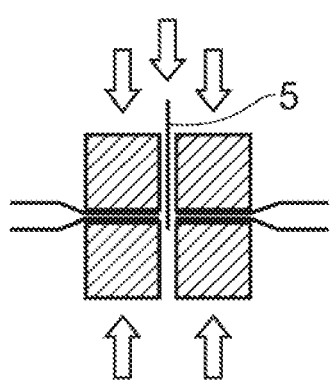
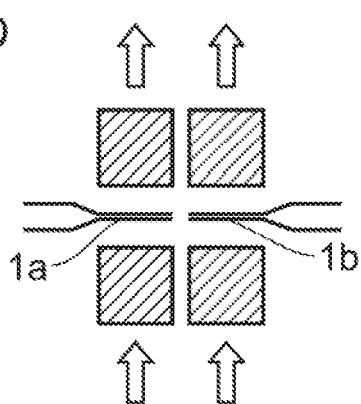

HEATSEAL

CROSS-REFERENCE TO RELATED APPLICATIONS

This application is a filing under 35 U.S.C. 371 of international application number PCT/EP2015/056919, filed Mar. 30, 2005, which claims priority to GB application number 1405591.7, filed Mar. 28, 2014, the entire disclosures of each of which are hereby incorporated by reference.

TECHNICAL FIELD OF THE INVENTION

The present invention relates to radiopharmaceuticals and more particularly to positron-emission tomography (PET) tracers. Specifically the present invention is concerned with the automated synthesis of PET tracers.

DESCRIPTION OF RELATED ART

PET tracer synthesis by definition includes handling of radioactive material and as such steps need to be taken to minimize operator exposure to this material. PET tracers are now routinely produced by automated radiosynthesizers, i.e. compact automated systems that perform the chemical synthesis steps required to convert externally-produced radioisotopes into a desired PET tracer. Automated radiosynthesizers located in a shielded enclosure (i.e. a hot cell made of lead) facilitate reduction in operator exposure by significantly reducing the number of manual steps required while at the same time ensuring reproducible radiosynthesis yields.

Commonly-used automated synthesizers are based on the use of a single-use consumable that interfaces with the synthesizer and which has a disposable fluid-path within which the chemistry takes place. This consumable may comprise a collection of parts requiring user assembly prior to or at the time of interfacing with the synthesizer, or may be a self-contained unit that a user can directly interface with the synthesizer without prior assembly. These consumables are commonly referred to as "kits", "cassettes" or "cartridges" and typically include disposable tubing, valves, syringes, vials, cartridges and filters fluidly connected together when in place on the synthesizer.

Once the automated radiochemical process has completed, the resulting radiolabelled product is transferred via tubing into a product collection vial or a so-called dispensing device used for fractioning of the bulk solution into multiple doses. The product outlet line may be extended if required by means of an extension tube passing out of the hot cell in which the automated synthesizer is installed and into a neighbouring hot cell where the PET tracer solution is collected for downstream processing. FIG. 1 shows the known FASTlab™ synthesizer with the arrow indicating the product outlet line. An extension line may be installed in between this outlet line and the product collection vial and is connected through screw type connectors such as Luer connectors.

Once the PET tracer synthesis is finished the automated synthesizer is set-up for the next production by removing the used cassette and mounting a new cassette. However, as the used cassette is contaminated with residues of radioactive compounds, it is either necessary to wait until the radioactivity has decayed to a safe level for manual removal, or, if its removal is desired soon after use, the cassette has to be removed in an automated fashion and discarded into a shielded waste container as quickly as possible to reduce radiation exposure to operator.

U.S. Pat. No. 7,235,216 refers to a mechanism whereby a used kit is automatically ejected and then dropped into a prepared receptacle in order to install a fresh cassette before waiting for the radioactivity to decay. Also, WO 2013/012 mentions automatic ejection of a cassette into a shielded waste container. Systems are therefore known comprising means to disconnect and release the cassette from the synthesizer with no or limited operator intervention.

The present inventors recognize some problems with the known configurations. Firstly, that disconnection of the cassette from the extension line leading to the product collection vial remains a manual step entailing radiation exposure to the operator. Also, that once the line is disconnected there is a risk of contamination of the hot cell and the operator with liquid radioactive material still contained in the outlet line. Furthermore, where there is a Luer lock connection of the outlet line to an extension line leading to the product collection vial in a neighboring hot cell, this can also be an issue because disconnection of this line requires manual operation in front of an open hot cell while there is still radiation present from the previous run.

There is therefore scope for an even further improved system.

SUMMARY OF THE INVENTION

The present invention relates to systems and methods to facilitate replacement between runs of a kit or cassette from an automated radiosynthesis device located in a hot cell. The method and apparatus of the invention enable automated disconnection of the outlet line by sealing the tubing hermetically by means of heat and by cutting the tubing where it is sealed in such a way that there is no risk of environmental contamination with radioactive material. The invention enables disconnection of the outlet line or extension line without manual intervention before opening the shielded enclosure, and consequently also enables full automated ejection into a shielded container without any manual intervention. Radiation exposure to the operator during removal of the kit is thereby reduced, if not eliminated. The potential for radioactive contamination within the hot cell is also reduced.

The method and apparatus of the present invention facilitate back-to-back runs by minimizing operator radiation exposure during cassette removal after a first run when there is still significant amount of residual radioactivity within the cell. This radiation comes from the used cassette but also from other sources inside the cell such as the synthesizer, PET isotope inlet line and waste lines.

BRIEF DESCRIPTION OF THE FIGURES

FIGS. 2A-2D show an example of a heat sealing arrangements suitable for use in the present invention.

DETAILED DESCRIPTION OF THE PREFERRED EMBODIMENTS

Figure 1:
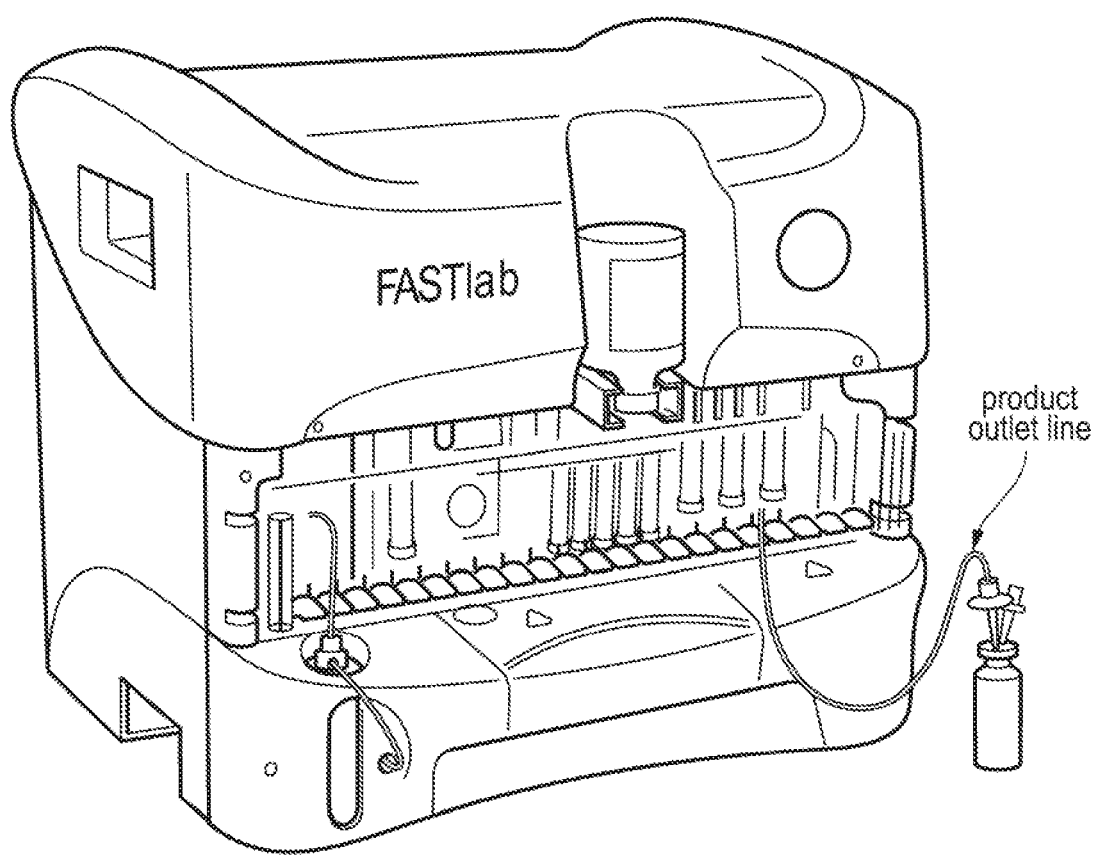
FIG. 1 shows an example of a commercially-available automated radiosynthesis device showing the product outlet line.

In one aspect the present invention provides a method comprising:
(i) providing a kit that can be fitted to an automated radiosynthesis device in order to synthesize a positron emission tomography (PET) tracer and one or more sections of thermoplastic tubing;
(ii) fitting said kit and said one or more sections of thermoplastic tubing to the automated radiosynthesis device;
(iii) introducing a PET isotope into said kit to carry out a radiochemical process to form a radiolabelled product;
(iv) transferring said radiolabelled product from said kit to a product collection device and/or a product processing device; and,
(v) heat sealing and cutting said one or more sections of thermoplastic tubing.

The term "kit" as used herein is intended to refer to a collection of materials and reagents suitable for use with an automated radiosynthesis device to manufacture a PET tracer. A typical kit will include all the non-radioactive materials and reagents required to complete the radiosynthesis, each contained in its own vial, with the PET isotope introduced at a later step. In one embodiment the kit will comprise a precursor compound and any other reactants and reagents required for the radiosynthesis, each contained in a vial or other suitable container. In one embodiment the kit itself will not include any reagents, in which case they are connected manually at the set-up of the process. Other components may include vials containing solvents in which labelling, deprotection, neutralization and purification may be suitably carried out, a reaction vessel, solid phase extraction cartridges suitable for example for post-labelling deprotection or purification. Thermoplastic tubing to fluidly connect the components of the kit together may be provided as an integral part of the kit or alternatively separately to the kit for assembly before use. The kit may be provided as separate parts that are assembled and connected just prior to or at the time of fitting to the automated radiosynthesis device. Alternatively, the kit may be provided as a single pre-assembled unit or "cassette" (also referred to as a "cartridge") that can be directly interfaced with the automated radiosynthesis device, for example those used with the FASTlab™ platform. It is preferred that said kit of the invention is a cassette.

The term "precursor compound" refers to a non-radioactive derivative of a PET tracer, designed so that chemical reaction with a convenient chemical form of a PET isotope occurs site-specifically, can be conducted in the minimum number of steps (ideally a single step), and without the need for significant purification (ideally no further purification), to give the desired PET tracer. Such precursor compounds are synthetic and can conveniently be obtained in good chemical purity. In some cases a precursor compound comprises one or more protecting groups aiming to prevent reaction of the PET isotope at the wrong site in the molecule. By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Third Edition, John Wiley & Sons, 1999).

The term "automated radiosynthesis" refers to a radiosynthesis that is performed without human intervention, i.e. a process that is driven and controlled by at least one machine and that is completed without the need of manual interference. Software programs are used to direct the steps carried out on a kit. There are several commercially-available examples of automated radiosynthesis devices, including Tracerlab MX™ and FASTlab™ (GE Healthcare), FDG-Plus Synthesizer (Bioscan) and Synthere (IBA).

A "PET tracer" is a biologically active chemical compound wherein at least one atom thereof is a PET isotope. Following administration to a subject, radioactive emissions from the PET isotope may be externally detected in order to provide an image of biochemical processes in said subject.

A "PET isotope" is an atom that emits positrons and that is suitable for use in PET imaging. Examples of PET isotopes include the positron-emitting non-metals $^{18}$F, $^{11}$C, $^{76}$Br and $^{124}$I as well as the positron-emitting metals $^{94m}$Tc, $^{86}$Y, $^{66}$Ga, $^{68}$Ga, $^{60}$Cu, $^{64}$Cu and $^{89}$Zr. Preferred PET isotopes include $^{18}$F, $^{11}$C and $^{68}$Ga.

The term "radiolabelled product" refers to the resultant reaction mixture obtained following reaction of the precursor compound and the PET isotope. This reaction mixture comprises the desired PET tracer, or a protected version thereof where a protected precursor compound is used. There may also be impurities present that need to be removed or at least substantially removed in one or more purification steps before obtaining the final PET tracer.

A "product collection device" generally refers simply to a vial in which the radiolabelled product is collected, either directly or subsequent to purification and/or other processing steps. In one embodiment said product collection device is a product collection vial.

A "product processing device" refers to any device used to evaluate or process the radiolabelled product in order to result in the final PET tracer. Non-limiting examples of product processing devices therefore include chromatography devices, dispensing devices and quality control devices.

A "product outlet line" refers to a conduit, typically a length of tubing that fluidly connects an outlet port on the kit to the product collection device and/or the product processing device. In one embodiment the product outlet line is formed completely from thermoplastic tubing. In another embodiment said product outlet line is just partly formed from thermoplastic tubing, e.g. the outlet line is connected to a piece of tubing made of thermoplastic material while the rest of the outlet line is made of another material. Connection of the outlet line to the thermoplastic tubing may be achieved e.g. through Luer connectors.

The term "thermoplastic tubing" refers to tubing made from a polymer that becomes pliable or mouldable above a specific temperature, and returns to a solid state upon cooling.

The term "heat sealing" refers to applying heat, and optionally also pressure, at defined position along the thermoplastic tubing in order to seal off the passageway of the tubing so that fluid can no longer pass through the sealed area. Cutting the tubing within the sealed area should result in two hermetically sealed ends so that there is no risk of environmental contamination with radioactive material. Heat sealing is used for many applications, including heat seal connectors, thermally activated adhesives, film media, plastic ports or foil sealing.

The term "cutting" refers to any process that cleanly divides the thermoplastic tubing at the area sealed in the heat sealing step.

Due to the radioactive nature of the processes, each of said radiosynthesis device, product collection device and product processing device is contained within a shielded enclosure such as a hot cell. Shielding is commonly ensured by the use of lead or in some cases materials such as concrete or tungsten.

The automated radiosynthesis device may be contained within a first shielded enclosure with the other devices, i.e. the product collection device and any product processing devices being contained within a second shielded enclosure. Particularly for this type of set up, although there may be need with others also, it may be necessary for the product outlet line to be extended by means of an extension line. The extension line is connected via screw-type connectors, for example Luer connectors. The tubing made of thermoplastic material may be the product outlet line, the extension line or an additional piece of tubing connected in between, upstream or downstream of these two lines and can be located anywhere between the outlet port of the cassette and the product collection device.

Ideally, the automated radiosynthesis device should be as close as possible to the product collection device and any product processing devices in order to have the simplest system set up, which in turn facilitates disconnection of a used kit since there will be less tubing to contend with. So for example all the equipment could be contained within shielded enclosures that are next to each other or even more favorably within one and the same shielded enclosure.

Non-limiting examples of $^{18}$F-labelled PET tracers currently produced in an automated fashion include [$^{18}$F] fluorodeoxyglucose ([$^{18}$F]FDG), [$^{18}$F]fluoromisonidazole, ([$^{18}$F]FMISO), [$^{18}$F]fluorothymidine ([$^{18}$F]FLT), [$^{18}$F]sodium fluoride ([$^{18}$F]NaF), [$^{18}$F]fluorohydroxymethylbutyl guanine ([$^{18}$F]FHBG), [$^{18}$F]fallypride, [$^{18}$F]fluoroarabinofuranosyl cytosine ([$^{18}$F]FAC), [$^{18}$F]fluoromethylarabinofuranosyluracil [$^{18}$F]FMAU, [$^{18}$F]fluoroethylarabinofuranosyluracil ([$^{18}$F]FEAU), N-succinimidyl 4-[$^{18}$F] fluorobenzoate ([$^{18}$F]SFB), [$^{18}$F]fluorocholine ([$^{18}$F]FCH), [$^{18}$F]fluorethylcholine ([$^{18}$F]FEC), [$^{18}$F]fluoromethylcholine ([$^{18}$F]FMC), [$^{18}$F]fluoroethyltyrosine ([$^{18}$F]FET), [$^{18}$F] fluoroestradiol ([$^{18}$F]FES), [$^{18}$F]fluorodihydroxyphenylalanine ([$^{18}$F]F-DOPA), 2-(1-(6-((2-[$^{18}$F]fluoroethyl)(methyl)amino)naphthalen-2-yl)ethylidene)malononitrile ([$^{18}$F] FDDNP), [$^{18}$F]fluoroazomycin arabinoside ([$^{18}$F]FAZA), [$^{18}$F]acetate. A number of $^{11}$C-labelled and $^{68}$Ga-labelled PET tracers have also been obtained using automated methods.

The primary aim of the present invention is to safely and effectively disconnect a used kit from the automated synthesis apparatus before dropping it into a shielded waste bin, as for example suggested in U.S. Pat. No. 7,235,216 and WO 2013/012. The heat sealing and cutting steps are therefore advantageously carried out in the shielded enclosure in which the automated radiosynthesis device is located. In this way, there is as little tubing as possible to be disposed of along with the kit, and also there will not be tubing having to potentially move from one shielded enclosure to another in order to dispose of the used kit.

Another major advantage is enabling full ejection of the cassette into a waste container. Without a means to disconnect the outlet tube, the used kit or cassette would be ejected into a waste container while the outlet tube remains connected to a product vial or dispensing device.

The present invention also presents the opportunity to selectively remove other components of the kit. For example, in a research setting it may be of interest to selectively remove the reaction vessel to measure yield, etc. Where the reaction vessel is fluidly connected within said kit by means of one or more reaction vessel lines and where these reaction vessel lines comprise thermoplastic tubing, the method of the invention may comprise the additional step carried out either before or after step (v) of heat sealing and then cutting said thermoplastic tubing of said one or more reaction vessel lines. In other embodiments the invention could also be used to disconnect other lines including without limitation the tubing connecting kit/cassette to enriched $^{18}$O water vial and the tubing connecting kit/cassette to waste container (into which all waste fluids from the process are drained).

The heat sealing and cutting step of the method of the invention may be carried out by:
(a) placing a portion of said thermoplastic tubing in a press;
(b) activating said press to compress said portion of tubing;
(c) heating said press to seal said portion of tubing by heat welding; and,
(d) cutting said sealed tubing within the portion of tubing sealed by step (c).

The press applies heat and pressure to the thermoplastic tubing in order to effect the heat sealing. Such devices are well-known in the field of packaging, e.g. bags and blisters in the food and pharmaceutical industry. A suitable press for the present invention comprises a relatively small heat sealer that can easily fit into a hot cell in which the automated radiosynthesis device, and potentially other post-radiolabelling devices, are located. The press typically comprises a heating element and is at least partially automated, e.g. by means of a timer or being foot-operated outside the hot cell. The direct contact method of heat sealing utilizes a constantly heated die or sealing bar to apply heat to a specific contact area or path to seal or weld the thermoplastics together. Operation of the heating element may be carried out by the release of a short burst of electricity through a resistance wire so that the heating element comes to a temperature effective to weld the thermoplastic tubing together at a defined point. The duration of heat sealing step must be selected carefully. If too short it will result in a weak seal and if too long the thermoplastic material will burn instead of melt and will also result in an inferior seal.

The temperature, pressure and duration of application will depend on the thermoplastic material in question. Non-limiting examples of material suitable for the thermoplastic tubing of the present invention include polypropylene (PP), polyethylene (PE), polyvinyl chloride (PVC), nylon, polytetrafluoroethylene (PTFE) and polyether ketone (PEEK). Polyolefin materials are preferred, such as PP and PE. The whole product outlet line could be made of the thermoplastic material but it is also envisaged that there could be only a piece of tubing made of such material and connected to the line upstream and downstream, e.g. via standard connectors such as Luer connectors.

The cutting step is achieved using a blade sufficiently sharp to cut through the heat-sealed section of the thermoplastic tubing. Suitably the cutting step is carried out in an automated fashion, e.g. by use of a pneumatically- or motor-driven system. Cutting of the sealed tube could be achieved by a blade or by means of a sharp heated element of the press.

A variety of configurations is possible. FIGS. 2A, 2B, 2C, and 2D, and 3A, 3B, and 3C illustrate some non-limiting examples.

In FIGS. 2A, 2B, 2C, and 2D, the tubing 1 to be sealed is inserted in FIG. 2A into a press comprising four press elements 2*a-d*, each having a press surface 3*a-d*, which may be flat as illustrated in FIG. 2A but may equally have different configurations, e.g. be curved, indented or rippled, as long as the surfaces function to seal the tubing 1 when brought together. The press elements 2*a-d* are arranged as two pairs 2*a*, 2*b* and 2*c*, 2*d* diametrically opposite each other around the tubing 1 with the flat press surfaces 3*a-d* directly facing each other and in parallel. In a different embodiment it could be envisaged that the press elements 2*a* and 2*b*, and similarly 2*c* and 2*d*, are joined together as a single element wherein the respective spacings 4*a* and 4*b* are instead slots between the two joined elements. Between each pair of press elements 2*a*, 2*b* and 2*c*, 2*d* is a spacing 4*a*, 4*b* sufficient for a blade 5 to pass therethrough. When the pairs of press elements 2*a*, 2*b* and 2*c*, 2*d* are brought together as in FIG. 2B the respective spacings 4*a*, 4*b* need to be aligned to define a passageway 4. In step B, the opposing pairs of surfaces 3*a*, 3*b* and 3*c*, 3*d* are brought together in parallel alignment so that they compress the tubing 1. Heating the press during compression acts to seal the tubing 1.

The cutting step of FIG. 2C can be carried out while the tubing 1 is still held within the press by passing the blade 5 through the passageway 4 defined by the aligned spacings 4*a*, 4*b* of the pairs of press elements 2*a*, 2*b* and 2*c*, 2*d*. The press is then released in in FIG. 2D to free the heat sealed and cut ends 1 *a*, 1 *b* of tubing.

Figure 3A:
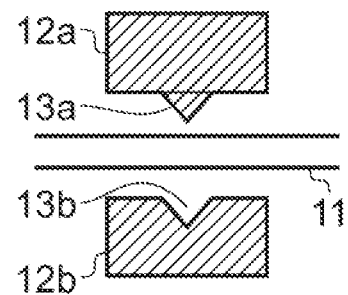
FIGS. 3A-3C show an example of a heat sealing arrangements suitable for use in the present invention.
Figure 3B:
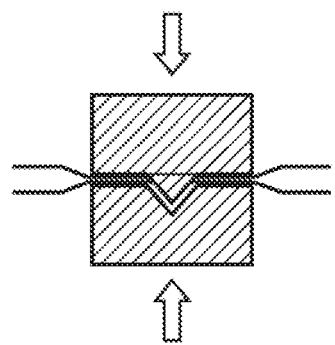
Figure 3C:
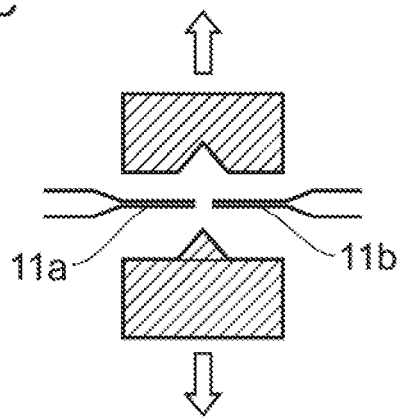

In FIGS. 3A, 3B, and 3C the press elements 12*a* and 12*b* are positioned at opposing sides of the tubing 11 as shown in FIG. 3A. However, in contrast to the arrangement of FIGS. 2A, 2B, 2C, and 2D, the press elements 12*a* and 12*b* do not have flat opposing surfaces but rather 12*a* has a sharp element 13*a* and 12*b* has a receiving element 13*b*. When press elements 12*a* and 12*b* are brought together sharp element 13*a* fits within receiving element 13*b* to effect cutting of the tubing 11 as shown in FIG. 3B. Heating takes place either before or concurrently with this cutting step, preferably before so that the cutting is carried out on cooled heat sealed tubing. In FIG. 3C, the press is released to free the heat sealed and cut ends 11*a* and 11 *b* of tubing.

Preferably cutting is carried out only once the heat-sealed portion of the thermoplastic tubing has cooled to ambient temperature so that the thermoplastic material is once again solid. However, it is envisaged that heat sealing and cutting may alternatively be carried out at the same time, such as with the configuration illustrated in FIGS. 3A, 3B, and 3C.

The heat sealing and cutting elements could be provided as an additional part of the automated radiosynthesis device, or offered as an add-on device.

In the method of the invention there may be additional processing steps carried out on the radiolabelled product prior to the transferring step, including:
 (a) removing any protecting groups where these are present;
 (b) removing excess PET isotope;
 (c) removing one or more impurities from said radiolabelled product.
These are well-known steps taken in order to arrive at an optimum PET tracer product.

Once the radiolabelled product has been synthesized and optionally further processed the subsequent method steps of:
 (vi) removing said kit from said automated radiosynthesis device; and then,
 (vii) disposing of said kit into a shielded waste container;
 may be carried out.

In another aspect, the present invention provides an apparatus comprising:
 (i) an automated radiosynthesis device;
 (ii) a kit that can be fitted to an automated radiosynthesis device in order to synthesize a PET tracer;
 (iii) one or more sections of thermoplastic tubing;
 (iv) a heat sealing and cutting device located proximal to said one or more sections of thermoplastic tubing.

Any feature of the apparatus of the invention having the same name as any feature of the method of the invention has the same meaning as provided herein for that feature for the method of the invention, including any preferred embodiments.

The invention claimed is:

1. A method comprising:
 (i) providing a kit that can be fitted to an automated radiosynthesis device in order to synthesise a positron emission tomography (PET) tracer and one or more sections of thermoplastic tubing, wherein a shielded enclosure contains the radiosynthesis device;
 (ii) fitting said kit and said one or more sections of thermoplastic tubing to the automated radiosynthesis device;
 (iii) introducing a PET isotope into said kit to carry out a radiochemical process to form a radiolabelled product;
 (iv) transferring said radiolabelled product from said kit to a product collection device and/or a product processing device; and,
 (v) heat sealing and cutting said one or more sections of thermoplastic tubing, wherein the heat sealing and cutting said one or more sections of thermoplastic tubing takes place within the shielded enclosure containing the radiosynthesis device.

2. The method as defined in claim 1 wherein the radiolabeled product is transferred from said kit to the product collection device in step (iv), and said product collection device is a product collection vial.

3. The method as defined in claim 1 wherein the radiolabeled product is transferred from said kit to the product processing device in step (iv), and said product processing device is a chromatography device, a dispensing device or a quality control device.

4. The method as defined in claim 1 wherein each of said radiosynthesis device, and product collection device and/or product processing device is contained within a shielded enclosure.

5. The method as defined in claim 4 wherein said shielded enclosure is a hot cell.

6. The method as defined in claim 5 wherein said automated radiosynthesis device is contained within a first shielded enclosure and said product collection device and/or said product processing device are contained within a second shielded enclosure.

7. The method as defined in claim 5 wherein said automated radiosynthesis device and said product collection device and/or said product processing device are contained within the same shielded enclosure.

8. The method as defined in claim 7 wherein said one or more sections of thermoplastic tubing comprise one or more of:
 (a) tubing connecting the kit to an enriched $^{18}O$ water vial;
 (b) tubing fluidly connecting a reaction vessel within said kit;
 (c) tubing comprised in a product outlet line;
 (d) tubing comprised in a product outlet extension line; or,
 (e) tubing connecting the kit to a waste container.

9. The method as defined in claim 8 wherein said one or more sections of thermoplastic tubing comprise (c) tubing comprised in a product outlet line, and said product outlet line is heat sealed in the shielded enclosure containing the radiosynthesis device.

10. The method as defined in claim 9 wherein said product outlet line is extended by means of an extension line.

11. The method as defined in claim 10 wherein said extension line is connected via screw-type connectors.

12. The method as defined in claim 11 wherein said screw-type connectors are Luer connectors.

13. The method as defined in claim 12 wherein said kit comprises said precursor compound contained in a vial.

14. The method as defined in claim 8 wherein said reaction vessel is fluidly connected within said kit by means of one or more reaction vessel lines wherein said reaction vessel lines comprise thermoplastic tubing.

15. The method as defined in claim 14 wherein said heat sealing and cutting is carried out by:
(a) placing a portion of said thermoplastic tubing in a press;
(b) activating said press to compress said portion of tubing;
(c) heating said press to seal said portion of tubing by heat welding; and,
(d) cutting said sealed tubing within the portion of tubing sealed by step (c).

16. The method as defined in claim 15 wherein said thermoplastic tubing is made from polypropylene (PP), polyethylene (PE), polyvinyl chloride (PVC), nylon, polytetrafluoroethylene (PTFE) or polyether ketone (PEEK).

17. The method as defined in claim 16 wherein said thermoplastic tubing is made from polypropylene (PP) or polyethylene (PE).

18. The method as defined in claim 17 wherein said PET isotope is $^{68}$Ga.

19. The method as defined in claim 17 wherein said PET isotope is $^{11}$C.

20. The method as defined in claim 17 wherein said PET isotope is $^{18}$F.

21. The method as defined in claim 20 wherein, prior to said transferring step (iv), one or more of the following steps is carried out on said radiolabelled product:
(a) removing any protecting groups where these are present;
(b) removing excess PET isotope;
(c) removing one or more impurities from said radiolabelled product.

22. The method as defined in claim 21 which comprises the subsequent steps of:
(vi) removing said kit from said automated radiosynthesis device; and then,
(vii) disposing of said kit into a shielded waste container.

23. An apparatus comprising:
(i) an automated radiosynthesis device, wherein a shielded enclosure contains the radiosynthesis device;
(ii) a kit that can be fitted to an automated radio synthesis device in order to synthesise a PET tracer;
(iii) one or more sections of thermoplastic tubing;
(iv) a heat sealing and cutting device located proximal to said one or more sections of thermoplastic tubing, wherein the heat sealing and cutting said one or more sections of thermoplastic tubing takes place within the shielded enclosure containing the radiosynthesis device.

24. The apparatus as defined in claim 23 wherein said one or more sections of thermoplastic tubing comprise one or more of:
(a) tubing connecting the kit to an enriched $^{18}$O water vial;
(b) tubing fluidly connecting a reaction vessel within said kit;
(c) tubing comprised in a product outlet line; and,
(d) tubing connecting the kit to a waste container.

25. The apparatus as defined in claim 24 wherein said one or more sections of thermoplastic tubing comprise (c) tubing comprised in a product outlet line, and said product outlet line is extended by means of an extension line.

26. The apparatus as defined in claim 25 wherein said extension line is connected via screw-type connectors.

27. The apparatus as defined in claim 26 wherein said screw-type connectors are Luer connectors.

28. The apparatus as defined in claim 27 wherein said kit comprises a precursor compound contained in a vial.

29. The apparatus as defined in claim 24 wherein said tubing fluidly connecting said reaction vessel comprises one or more reaction vessel lines.

30. The method as defined in claim 29 wherein said thermoplastic tubing is made from polypropylene (PP), polyethylene (PE), polyvinyl chloride (PVC), nylon, polytetrafluoroethylene (PTFE) or polyether ketone (PEEK).

31. The apparatus defined in claim 30 wherein said thermoplastic tubing is made from polypropylene (PP) or polyethylene (PE).

* * * * *